United States Patent
Smit et al.

(10) Patent No.: US 12,390,124 B2
(45) Date of Patent: Aug. 19, 2025

(54) SYSTEMS AND METHODS FOR NON-CONTACT RESPIRATORY MONITORING

(71) Applicant: Covidien LP, Mansfield, MA (US)

(72) Inventors: Philip C. Smit, Hamilton (GB); Paul S. Addison, Scotland (GB); Dominique Jacquel, Edinburgh (GB)

(73) Assignee: Covidien LP, Mansfield, MA (US)

( * ) Notice: Subject to any disclaimer, the term of this patent is extended or adjusted under 35 U.S.C. 154(b) by 776 days.

(21) Appl. No.: 17/583,583

(22) Filed: Jan. 25, 2022

(65) Prior Publication Data

US 2022/0233096 A1 Jul. 28, 2022

Related U.S. Application Data

(60) Provisional application No. 63/142,298, filed on Jan. 27, 2021.

(51) Int. Cl.
*A61B 5/08* (2006.01)
*A61B 5/00* (2006.01)
(Continued)

(52) U.S. Cl.
CPC .......... *A61B 5/0816* (2013.01); *A61B 5/0077* (2013.01); *A61B 5/091* (2013.01); *A61B 5/1128* (2013.01); *A61B 5/113* (2013.01)

(58) Field of Classification Search
None
See application file for complete search history.

(56) References Cited

U.S. PATENT DOCUMENTS

| 5,107,845 A | 4/1992 | Guern et al. |
| 5,408,998 A | 4/1995 | Mersch |

(Continued)

FOREIGN PATENT DOCUMENTS

| CA | 2234191 A1 | 10/1998 |
| CN | 106725410 A | 5/2017 |

(Continued)

OTHER PUBLICATIONS

Lawrence, E., et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.

(Continued)

*Primary Examiner* — Meredith Weare
(74) *Attorney, Agent, or Firm* — Draft Masters IP, LLC

(57) ABSTRACT

Methods and systems for non-contact monitoring of a patient to determine respiratory parameters such as respiration rate, tidal volume, minute volume, oxygen saturation, and other parameters such as motion or activity. The systems and methods receive a first, video signal from the patient and from that extract a distance or depth signal from the relevant area to calculate the parameter(s) from the depth signal. The systems and methods also receive a second, light intensity signal from an IR feature projected onto the patient, and from that calculate the parameter(s) from the light intensity signal. The parameter(s) from the two signals can be combined or compared to provide a qualified output parameter.

16 Claims, 7 Drawing Sheets

(51) Int. Cl.
  *A61B 5/091* (2006.01)
  *A61B 5/11* (2006.01)
  *A61B 5/113* (2006.01)

(56) References Cited

U.S. PATENT DOCUMENTS

| | | | |
|---|---|---|---|
| 5,704,367 A | 1/1998 | Ishikawa et al. | |
| 5,800,360 A | 9/1998 | Kisner et al. | |
| 5,995,856 A | 11/1999 | Mannheimer et al. | |
| 6,241,684 B1 | 6/2001 | Amano et al. | |
| 6,668,071 B1 | 12/2003 | Minkin et al. | |
| 6,920,236 B2 | 7/2005 | Prokoski | |
| 7,431,700 B2 | 10/2008 | Aoki et al. | |
| 7,558,618 B1 | 7/2009 | Williams | |
| 7,630,537 B2 * | 12/2009 | Sato | A61B 5/0064 |
| | | | 348/E5.029 |
| 8,149,273 B2 | 4/2012 | Liu et al. | |
| 8,754,772 B2 | 6/2014 | Horng et al. | |
| 8,792,969 B2 | 7/2014 | Bernal et al. | |
| 8,971,985 B2 | 3/2015 | Bernal et al. | |
| 9,226,691 B2 | 1/2016 | Bernal et al. | |
| 9,282,725 B2 | 3/2016 | Jensen-Jarolim et al. | |
| 9,301,710 B2 | 4/2016 | Mestha et al. | |
| 9,402,601 B1 | 8/2016 | Berger et al. | |
| 9,436,984 B2 | 9/2016 | Xu et al. | |
| 9,443,289 B2 | 9/2016 | Xu et al. | |
| 9,504,426 B2 | 11/2016 | Kyal et al. | |
| 9,508,141 B2 | 11/2016 | Khachaturian et al. | |
| 9,607,138 B1 | 3/2017 | Baldwin et al. | |
| 9,662,022 B2 | 5/2017 | Kyal et al. | |
| 9,693,693 B2 | 7/2017 | Farag et al. | |
| 9,693,710 B2 | 7/2017 | Mestha et al. | |
| 9,697,599 B2 | 7/2017 | Prasad et al. | |
| 9,750,461 B1 | 9/2017 | Telfort | |
| 9,839,756 B2 | 12/2017 | Klasek | |
| 9,943,371 B2 | 4/2018 | Bresch et al. | |
| 10,213,540 B2 | 2/2019 | Burbank et al. | |
| 10,278,585 B2 | 5/2019 | Ferguson et al. | |
| 10,376,147 B2 | 8/2019 | Wood et al. | |
| 10,398,353 B2 | 9/2019 | Addison et al. | |
| 10,447,972 B2 | 10/2019 | Patil | |
| 10,489,912 B1 | 11/2019 | Brailovskiy | |
| 10,523,852 B2 | 12/2019 | Tzvieli et al. | |
| 10,588,779 B2 | 3/2020 | Vorhees et al. | |
| 10,589,916 B2 | 3/2020 | Mcrae | |
| 10,650,585 B2 | 5/2020 | Kiely | |
| 10,667,723 B2 | 6/2020 | Jacquel et al. | |
| 10,702,188 B2 | 7/2020 | Addison et al. | |
| 10,729,357 B2 | 8/2020 | Larson et al. | |
| 10,874,331 B2 | 12/2020 | Kaiser et al. | |
| 10,937,296 B1 | 3/2021 | Kukreja et al. | |
| 10,939,824 B2 | 3/2021 | Addison et al. | |
| 10,939,834 B2 | 3/2021 | Khwaja et al. | |
| 10,966,059 B1 | 3/2021 | Dayal et al. | |
| 11,311,252 B2 | 4/2022 | Jacquel et al. | |
| 11,315,275 B2 | 4/2022 | Addison et al. | |
| 11,317,828 B2 | 5/2022 | Addison et al. | |
| 11,350,850 B2 | 6/2022 | Jacquel et al. | |
| 11,850,026 B2 | 12/2023 | Levi et al. | |
| 2002/0137464 A1 | 9/2002 | Dolgonos et al. | |
| 2004/0001633 A1 | 1/2004 | Caviedes | |
| 2004/0258285 A1 | 12/2004 | Hansen et al. | |
| 2005/0027205 A1 * | 2/2005 | Tarassenko | A61B 5/0816 |
| | | | 600/529 |
| 2005/0203348 A1 | 9/2005 | Shihadeh et al. | |
| 2007/0116328 A1 | 5/2007 | Sablak et al. | |
| 2008/0001735 A1 | 1/2008 | Tran | |
| 2008/0108880 A1 | 5/2008 | Young et al. | |
| 2008/0279420 A1 | 11/2008 | Masticola et al. | |
| 2008/0295837 A1 | 12/2008 | McCormick et al. | |
| 2009/0024012 A1 | 1/2009 | Li et al. | |
| 2009/0141124 A1 | 6/2009 | Liu et al. | |
| 2009/0304280 A1 | 12/2009 | Aharoni et al. | |
| 2010/0210924 A1 | 8/2010 | Parthasarathy et al. | |
| 2010/0236553 A1 | 9/2010 | Jafari et al. | |
| 2010/0249630 A1 | 9/2010 | Droitcour et al. | |
| 2010/0324437 A1 | 12/2010 | Freeman et al. | |
| 2011/0144517 A1 | 6/2011 | Cervantes | |
| 2011/0150274 A1 | 6/2011 | Patwardhan et al. | |
| 2012/0065533 A1 | 3/2012 | Carrillo et al. | |
| 2012/0075464 A1 | 3/2012 | Derenne et al. | |
| 2012/0195473 A1 | 8/2012 | De Haan et al. | |
| 2012/0243797 A1 | 9/2012 | Di Venuto Dayer et al. | |
| 2013/0053718 A1 * | 2/2013 | Hung | A61B 5/1128 |
| | | | 600/534 |
| 2013/0073312 A1 | 3/2013 | Thompson et al. | |
| 2013/0267873 A1 | 10/2013 | Fuchs | |
| 2013/0271591 A1 | 10/2013 | Van Leest et al. | |
| 2013/0272393 A1 | 10/2013 | Kirenko et al. | |
| 2013/0275873 A1 | 10/2013 | Shaw et al. | |
| 2013/0324830 A1 | 12/2013 | Bernal et al. | |
| 2013/0324875 A1 * | 12/2013 | Mestha | A61B 5/1077 |
| | | | 600/534 |
| 2013/0324876 A1 * | 12/2013 | Bernal | A61B 5/1135 |
| | | | 600/538 |
| 2014/0023235 A1 | 1/2014 | Cennini et al. | |
| 2014/0052006 A1 | 2/2014 | Lee et al. | |
| 2014/0053840 A1 | 2/2014 | Liu | |
| 2014/0073860 A1 | 3/2014 | Urtti | |
| 2014/0139405 A1 | 5/2014 | Ribble et al. | |
| 2014/0140592 A1 | 5/2014 | Lasenby et al. | |
| 2014/0235976 A1 | 8/2014 | Bresch et al. | |
| 2014/0267718 A1 | 9/2014 | Govro et al. | |
| 2014/0272860 A1 | 9/2014 | Peterson et al. | |
| 2014/0275832 A1 | 9/2014 | Muehlsteff et al. | |
| 2014/0276104 A1 | 9/2014 | Tao et al. | |
| 2014/0303503 A1 * | 10/2014 | Rocque | A61B 5/1135 |
| | | | 600/407 |
| 2014/0330336 A1 | 11/2014 | Errico et al. | |
| 2014/0334697 A1 | 11/2014 | Kersten et al. | |
| 2014/0358017 A1 | 12/2014 | Op Den Buijs et al. | |
| 2014/0378810 A1 | 12/2014 | Davis et al. | |
| 2014/0379369 A1 | 12/2014 | Kokovidis et al. | |
| 2015/0003723 A1 | 1/2015 | Huang et al. | |
| 2015/0068069 A1 | 3/2015 | Tran et al. | |
| 2015/0087997 A1 * | 3/2015 | Haider | A61B 5/0077 |
| | | | 600/476 |
| 2015/0094597 A1 | 4/2015 | Mestha et al. | |
| 2015/0131880 A1 | 5/2015 | Wang et al. | |
| 2015/0157269 A1 | 6/2015 | Lisogurski et al. | |
| 2015/0198707 A1 | 7/2015 | Al-Alusi | |
| 2015/0223731 A1 | 8/2015 | Sahin | |
| 2015/0238150 A1 | 8/2015 | Subramaniam | |
| 2015/0265187 A1 | 9/2015 | Bernal et al. | |
| 2015/0282724 A1 | 10/2015 | McDuff et al. | |
| 2015/0286779 A1 | 10/2015 | Bala et al. | |
| 2015/0301590 A1 | 10/2015 | Furst et al. | |
| 2015/0317814 A1 | 11/2015 | Johnston et al. | |
| 2015/0379370 A1 | 12/2015 | Clifton et al. | |
| 2016/0000335 A1 | 1/2016 | Khachaturian et al. | |
| 2016/0049094 A1 | 2/2016 | Gupta et al. | |
| 2016/0082222 A1 | 3/2016 | Garcia Molina et al. | |
| 2016/0140828 A1 | 5/2016 | Deforest | |
| 2016/0143598 A1 | 5/2016 | Rusin et al. | |
| 2016/0151022 A1 | 6/2016 | Berlin et al. | |
| 2016/0156835 A1 | 6/2016 | Ogasawara et al. | |
| 2016/0174887 A1 | 6/2016 | Kirenko et al. | |
| 2016/0210747 A1 | 7/2016 | Hay et al. | |
| 2016/0235344 A1 | 8/2016 | Auerbach | |
| 2016/0253812 A1 * | 9/2016 | Grossinger | G06T 19/006 |
| | | | 356/614 |
| 2016/0310084 A1 | 10/2016 | Banerjee et al. | |
| 2016/0317041 A1 | 11/2016 | Porges et al. | |
| 2016/0345931 A1 | 12/2016 | Xu et al. | |
| 2016/0367186 A1 | 12/2016 | Freeman et al. | |
| 2016/0371833 A1 * | 12/2016 | Prasad | A61B 5/1128 |
| 2017/0007342 A1 | 1/2017 | Kasai et al. | |
| 2017/0007795 A1 | 1/2017 | Pedro et al. | |
| 2017/0055877 A1 | 3/2017 | Niemeyer | |
| 2017/0065484 A1 | 3/2017 | Addison et al. | |
| 2017/0071508 A1 * | 3/2017 | Kaiser | A61B 5/0064 |
| 2017/0071516 A1 | 3/2017 | Bhagat et al. | |
| 2017/0095215 A1 | 4/2017 | Watson et al. | |
| 2017/0095217 A1 | 4/2017 | Hubert et al. | |

(56) References Cited

U.S. PATENT DOCUMENTS

| | | | |
|---|---|---|---|
| 2017/0119340 A1 | 5/2017 | Nakai et al. |
| 2017/0147772 A1 | 5/2017 | Meehan et al. |
| 2017/0164904 A1 | 6/2017 | Kirenko |
| 2017/0172434 A1 | 6/2017 | Amelard et al. |
| 2017/0173262 A1 | 6/2017 | Veltz |
| 2017/0238805 A1 | 8/2017 | Addison et al. |
| 2017/0238842 A1 | 8/2017 | Jacquel et al. |
| 2017/0311887 A1 | 11/2017 | Leussler et al. |
| 2017/0319114 A1 | 11/2017 | Kaestle |
| 2018/0042486 A1 | 2/2018 | Yoshizawa et al. |
| 2018/0042500 A1 | 2/2018 | Liao et al. |
| 2018/0049669 A1 | 2/2018 | Vu et al. |
| 2018/0053392 A1 | 2/2018 | White et al. |
| 2018/0104426 A1 | 4/2018 | Oldfield et al. |
| 2018/0106897 A1 | 4/2018 | Shouldice et al. |
| 2018/0169361 A1 | 6/2018 | Dennis et al. |
| 2018/0217660 A1 | 8/2018 | Dayal et al. |
| 2018/0228381 A1 | 8/2018 | Leboeuf et al. |
| 2018/0303351 A1 | 10/2018 | Mestha et al. |
| 2018/0310844 A1 | 11/2018 | Tezuka et al. |
| 2018/0325420 A1 | 11/2018 | Gigi |
| 2018/0333050 A1 | 11/2018 | Greiner et al. |
| 2018/0333102 A1 | 11/2018 | De Haan et al. |
| 2018/0352150 A1 | 12/2018 | Purwar et al. |
| 2019/0029604 A1* | 1/2019 | Jones ................ A61B 5/7278 |
| 2019/0050985 A1 | 2/2019 | Den Brinker et al. |
| 2019/0075257 A1* | 3/2019 | Ayyagari ............ G01S 7/4816 |
| 2019/0090785 A1* | 3/2019 | Heinrich ............ A61B 5/0075 |
| 2019/0133499 A1 | 5/2019 | Auerbach |
| 2019/0142274 A1 | 5/2019 | Addison et al. |
| 2019/0199970 A1 | 6/2019 | Greiner et al. |
| 2019/0209046 A1* | 7/2019 | Addison ............ A61B 5/1135 |
| 2019/0209083 A1 | 7/2019 | Wu et al. |
| 2019/0307365 A1 | 10/2019 | Addison et al. |
| 2019/0311101 A1 | 10/2019 | Nienhouse |
| 2019/0343480 A1 | 11/2019 | Shute et al. |
| 2019/0380599 A1 | 12/2019 | Addison et al. |
| 2019/0380807 A1 | 12/2019 | Addison et al. |
| 2020/0046302 A1 | 2/2020 | Jacquel et al. |
| 2020/0138336 A1* | 5/2020 | Shim .................. A61B 5/1135 |
| 2020/0187827 A1 | 6/2020 | Addison et al. |
| 2020/0196915 A1* | 6/2020 | Rabb .................. A61B 5/0816 |
| 2020/0202154 A1 | 6/2020 | Wang et al. |
| 2020/0205734 A1 | 7/2020 | Mulligan et al. |
| 2020/0237225 A1 | 7/2020 | Addison et al. |
| 2020/0242790 A1 | 7/2020 | Addison et al. |
| 2020/0250406 A1 | 8/2020 | Wang et al. |
| 2020/0253560 A1 | 8/2020 | De Haan |
| 2020/0279464 A1 | 9/2020 | Llewelyn |
| 2020/0289024 A1 | 9/2020 | Addison et al. |
| 2020/0329976 A1 | 10/2020 | Chen et al. |
| 2020/0367762 A1* | 11/2020 | Wallace ................. A61B 5/145 |
| 2020/0409383 A1 | 12/2020 | Maunder |
| 2021/0068670 A1 | 3/2021 | Redtel |
| 2021/0142874 A1 | 5/2021 | Llewelyn |
| 2021/0153746 A1 | 5/2021 | Addison et al. |
| 2021/0201517 A1 | 7/2021 | Yang et al. |
| 2021/0233631 A1 | 7/2021 | Llewelyn |
| 2021/0235992 A1 | 8/2021 | Addison |
| 2021/0295662 A1 | 9/2021 | Bugbee et al. |
| 2021/0313075 A1 | 10/2021 | McNamara et al. |
| 2022/0211296 A1 | 7/2022 | Addison et al. |
| 2023/0122367 A1 | 4/2023 | Tesar |

FOREIGN PATENT DOCUMENTS

| | | |
|---|---|---|
| CN | 111728602 A | 10/2020 |
| CN | 112233813 A | 1/2021 |
| DE | 19741982 A1 | 10/1998 |
| EP | 2793189 B1 | 11/2016 |
| EP | 2428162 B1 | 8/2017 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2004173010 A | 6/2004 |
| JP | 2004283373 A | 10/2004 |
| JP | 3744778 B2 | 12/2005 |
| JP | 2009544080 A | 12/2009 |
| JP | 2011130996 A | 7/2011 |
| KR | 101644843 B1 | 8/2016 |
| RS | 20120373 A1 | 4/2014 |
| WO | 2004100067 A2 | 11/2004 |
| WO | 2005079658 A2 | 9/2005 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017100188 A2 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | WO-2019157190 A1 * | 8/2019 ........... A61B 5/0077 |
| WO | 2019240991 A1 | 12/2019 |
| WO | 2020033613 A1 | 2/2020 |
| WO | 2021044240 A1 | 3/2021 |

OTHER PUBLICATIONS

Liu, H., et al., "A Novel Method Based on Two Cameras for Accurate Estimation of Arterial Oxygen Saturation", BioMedical Engineering Online, vol. 14, No. 52, 2015, 18 pages.

Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Liu, C., et al., "Motion Magnification", ACM Transactions on Graphics (TOG), vol. 24, No. 3, 2005, pp. 519-526, 8 pages.

Lv, et al., "Class Energy Image Analysis for Video Sensor-Based Gait Recognition: A Review", Sensors, No. 15, 2015, pp. 932-964, 33 pages.

McDuff, Daniel J., et al., "A Survey of Remote Optical Photoplethysmographic Imaging Methods", IEEE 987-1-4244-0270-1/15, 2015, pp. 6398-6404, 7 pages.

Mestha, L.K., et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.

Mukherjee, S., et al., "Patient health management system using e-health monitoring architecture", IEEE, International Advance Computing Conference (IACC), 978-1-4799-2572-8/14, Feb. 21, 2014, pp. 400-405, 6 pages.

Nguyen, et al., "3D shape, deformation and vibration measurements using infrared Kinect sensors and digital image correlation", Applied Optics, vol. 56, No. 32, Nov. 10, 2017, 8 pages.

Ni, et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.

Nisar, et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.

Pereira, C., et al., "Noncontact Monitoring of Respiratory Rate in Newborn Infants Using Thermal Imaging", IEEE Transactions on Biomedical Engineering, Aug. 23, 2018, 10 pages.

Poh, et al., "Advancements in Noncontact, Multiparameter Physiological Measurements Using a Webcam", IEEE Transactions on Biomedical Engineering, vol. 58, No. 1, Jan. 2011, pp. 7-11, 5 pages.

Poh, et al., "Non-contact, automated cardiac pulse measurements using video imaging and blind source separation", Opt. Express 18, 2010, pp. 10762-10774, 14 pages.

(56) References Cited

OTHER PUBLICATIONS

Povsic, Klemen, et al., "Real-Time 3D visualization of the thoraco-abdominal surface during breathing with body movement and deformation extraction", Physiological Measurement, vol. 36, No. 7, May 28, 2015, pp. 1497-1516, 22 pages.
Prochazka, et al., "Microsoft Kinect Visual and Depth Sensors for Breathing and Heart Rate Analysis", Senors, vol. 16, No. 7, Jun. 28, 2016, 11 pages.
Rajan, V., et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.
Rajan, V., et al., "Dependency Clustering of Mixed Data with Gaussian Mixture Copulas", 25th International Joint Conference on Artificial Intelligence IJCAI, New York, USA, 2016, pp. 1967-1973, 7 pages.
Reisner, A., et al., "Utility of the Photoplethysmogram in Circulatory Monitoring", American Society of Anesthesiologist, May 2008, pp. 950-958, 9 pages.
Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622, 12 pages.
Rubinstein, M, "Analysis and Visualization of Temporal Variations in Video", Department of Electrical Engineering and Computer Science, Massachusetts Institute of Technology, Feb. 2014, 118 pages.
Scalise, Lorenzo, et al., "Heart rate measurement in neonatal patients using a webcamera", Department of Industrial Engineering and Mathematical Science, Italy, 978-1-4673-0882-3/12, EEE, 2012, 4 pages.
Schaerer, J., et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.
Sengupta, A., et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.
Shah, Nitin, et al., "Performance of three new-generation pulse oximeters during motion and low perfursion in volunteers", Journal of Clinical Anesthesia, No. 24, 2012, pp. 385-391, 7 pages.
Shao, Dangdang, et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.
Shrivastava, H., et al., "Classification with Imbalance: A Similarity-based Method for Predicting Respiratory Failure", IEEE International Conference on Bioinformatics and Biomedicine (IEEE BIBM2015), Washington, DC, USA, 2015, pp. 707-714, 8 pages.
Srinivas, J., et al., "A Mutual Authentication Framework for Wireless Medical Sensor Networks", Journal of Medical Systems, 41:80, 2017, pp. 1-19, 19 pages.
Sun, Yu, et al., "Motion-compensated noncontact imaging photoplethysmography to monitor cardiorespiratory status during exercise", Journal of Biomedical Optics, vol. 16, No. 7, Jul. 1, 2011, 10 pages.
Sun, Yu, et al., "Noncontact imaging photoplethysmography to effectively access pulse rate variability", Journal of Biomedical Optics, vol. 18(6), Jun. 2013, 10 pages.
Tamura, et al., "Wearable Photoplethysmographic Sensors-Past & Present", Electronics, vol. 3, 2014, pp. 282-302, 21 pages.
Tarassenko, L., et al., "Non-contact video-based vital sign monitoring using ambient light and auto-regressive models", Institute of Physics and Engineering in Medicine, vol. 35, 2014, pp. 807-831, 26 pages.
Teichmann, D., et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.
Verkruysee, Wim, et al., "Calibration of Contactless Pulse Oximetry", Anesthesia & Analgesia, vol. 124, No. 1, Jan. 2017, pp. 136-145, 10 pages.
Villarroel, Mauricio, et al., "Continuous non-contact vital sign monitoring in neonatal intensive care unit", Healthcare Technology Letters, vol. 1, Issue 3, 2014, pp. 87-91, 5 pages.
Wadhwa, N., et al., "Phase-Based Video Motion Processing", MIT Computer Science and Artificial Intelligence Lab, Jul. 2013, 9 pages.
Wadhwa, N., et al., "Riesz pyramids for fast phase-based video magnification", In Proc. of IEEE International Conference on Computational Photography (ICCP), Santa Clara, CA, 2014, 10 pages.
Wang, W., et al., "Exploiting spatial redundancy of image sensor for motion robust rPPG", IEEE Transactions on Biomedical Engineering, vol. 62, No. 2, 2015, pp. 415-425, 11 pages.
Wu, H.Y., et al., "Eulerian video magnifcation for revealing subtle changes in the world", ACM Transactions on Graphics (TOG), vol. 31, No. 4, 2012, pp. 651-658, 8 pages.
Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.
Zaunseder, et al., "Spatio-temporal analysis of blood perfusion by imaging photoplethysmography", Progress in Biomedical Optics and Imaging, SPIE-International Society for Optical Engineering, vol. 10501, Feb. 20, 2018, 15 pages.
Zhou, J., et al., "Maximum parsimony analysis of gene copy number changes in tumor phylogenetics", 15th International Workshop on Algorithms in Bioinformatics WABI 2015, Atlanta, USA, 2015, pp. 108-120, 13 pages.
"European Search Report", European Application No. 17156334.9, Applicant: Covidien LP, Aug. 23, 2017, 10 pages.
"European Search Report", European Patent Application No. 17156337.2, Applicant: Covidien LP, Aug. 23, 2017, 10 pages.
"International Search Report and Written Opinion", International Application No. PCT/US2021/015669, Apr. 12, 2021, 15 pages.
"International Search Report and Written Opinion", International Application No. PCT/US2018/060648, Jan. 28, 2019, 17 pages.
"International Search Report and Written Opinion", International Application No. PCT/US2018/065492, Mar. 8, 2019, 12 pages.
"International Search Report and Written Opinion", International Application No. PCT/US 19/035433, Nov. 11, 2019, 17 pages.
"International Search Report and Written Opinion", International Application No. PCT/US2019/045600, Oct. 23, 2019, 19 pages.
"Invitation to Pay Additional Fees and Partial International Search Report", International Application No. PCT/US2019/035433, Sep. 13, 2019, 16 pages.
"Medical Electrical Equipment, Part 2-61: Particular requirements for basic safety and essential performance of pulse oximeter equipment", BSI Standards Publication, BS EN ISO 80601-2-61, 2011, 98 pages.
Aarts, Lonneke A.M., et al., "Non-contact heart rate monitoring utilizing camera photoplethysmography in neonatal Intensive care unit—A Pilot Study", Early Human Development 89, 2013, pp. 943-948, 6 pages.
Abbas, A.K., et al., "Neonatal non-contact respiratory monitoring based on real-time infrared thermography", Biomed. Eng. Online, vol. 10, No. 93, 2011, 17 pages.
Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.
Addison, Paul S., et al., "Developing an algorithm for pulse oximetry derived respirator rate (RRoxi): a healthy volunteer study", J Clin comput, No. 26, 2012, pp. 45-51, 7 pages.
Addison, Paul S., et al., "Pulse oximetry-derived respiratory rate in general care floor patients", J. Clin Monit Comput, No. 29, 2015, pp. 113-120, 8 pages.

(56) References Cited

OTHER PUBLICATIONS

Addison, P.S., et al., "Video-based Heart Rate Monitoring across a Range of Skin Pigmentations during an Acute Hypoxic Challenge", J Clin Monit Comput, vol. 9, Nov. 9, 2017, 15 pages.

Amazon, "Dockem Koala Tablet Wall Mount Dock for iPad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.

Amelard, et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.

Armanian, A. M., "Caffeine administration to prevent apnea in very premature infants", Pediatrics & Neonatology, 57 (5), 2016, pp. 408-412, 5 pages.

Barone, S, et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.

Barone, S, et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.

Bhattacharya, S., et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.

Bhattacharya, S., et al., "Unsupervised learning using Gaussian Mixture Copula models", 21st International Conference on Computational Statistics (COMPSTAT 2014), Geneva, Switzerland, 2014, pp. 523-530, 8 pages.

Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.

Bousefsaf, Frederic, et al., "Continuous wavelet filtering on webcam photoplethysmographic signals to remotely assess the instantaneous heart rate", Biomedical Signal Processing and Control 8, 2013, pp. 568-574, 7 pages.

Bruser, C., et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.

Cennini, Giovanni, et al., "Heart rate monitoring via remote photoplethysmography with motion artifacts reduction", Optics Express, vol. 18, No. 5, Mar. 1, 2010, pp. 4867-4875, 9 pages.

Colantonio, S., et al., "A smart mirror to promote a healthy lifestyle", Biosystems Engineering. vol. 138, Innovations in Medicine and Healthcare, Oct. 2015, pp. 33-43, 11 pages.

Cooley, et al., "An Alorithm for the Machine Calculation of Complex Fourier Series", Aug. 17, 1964, pp. 297-301, 5 pages.

Di Fiore, J.M., et al., "Intermittent hypoxemia and oxidative stress in preterm infants", Respiratory Physiology & Neurobiology, No. 266, 2019, pp. 121-129, 25 pages.

Fei, J., et al., "Thermistor at a distance: unobtrusive measurement of breathing", IEEE Transactions on Biomedical Engineering, vol. 57, No. 4, 2010, pp. 968-998, 11 pages.

Feng, Litong, et al., "Dynamic ROI based on K-means for remote photoplethysmography", IEE International Conference on Accoustics, Speech and Signal Processing (ICASSP), Apr. 2015, pp. 1310-1314, 5 pages.

Fischer, et al., "ReMoteCare: Health Monitoring with Streaming Video," OCMB '08, 7th International Conference on Mobile Business, IEEE, Piscataway, NJ,, Jul. 7, 2008, pp. 280-286.

George, et al., "Respiratory Rate Measurement From PPG Signal Using Smart Fusion Technique", International Conference on Engineering Trends and Science & Humanities (ICETSH-2015), 2015, 5 pages.

Goldman, L.J., "Nasal airflow and thoracoabdominal motion in children using infrared thermographic video processing", Pediatric Pulmonology, vol. 47, No. 5, 2012, pp. 476-486, 11 pages.

Grimm, T., et al., "Sleep position classification from a depth camera using bed aligned maps", 23rd International Conference on Pattern Recognition (ICPR), Dec. 2016, pp. 319-324, 6 pages.

Gsmarena, "Apple iPad Pro 11 (2018)", https://www.gsmarena.com/apple_ipad_pro_11_(2018)-9386.pjp, viewed on Nov. 16, 2021, 1 page.

Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.

Han, J., et al., "Visible and infrared image registration in man-made environments employing hybrid visuals features", Pattern Recognition Letters, vol. 34, No. 1, 2013, pp. 42-51, 10 pages.

Huddar, V., et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.

Hyvarinen, A., et al., "Independent Component Analysis: Algorithms and Applications", Neural Networks, vol. 13, No. 4, 2000, pp. 411-430, 31 pages.

Javadi, M., et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.

Jopling, M. W., et al., "Issues in the Laboratory Evaluation of Pulse Oximeter Performance", Anesth. Analg., No. 94, 2002, pp. S62-S68, 7 pages.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.

Klaessens, J.H.G.M., et al., "Non-invasive skin oxygenation imaging using a multi-spectral camera system: Effectiveness of various concentration algorithms applied on human skin", Proc. of SPIE, vol. 7174 717408-1, 2009, 14 pages.

Kong, Lingqin, et al., "Non-contact detection of oxygen saturation based on visible light imaging device using ambient light", Optics Express, vol. 21, No. 15, Jul. 29, 2013, pp. 17646-17471, 8 pages.

Kortelainen, J.M., et al., "Sleep staging based on signals acquired through bed sensor", IEEE Transactions on Informational Technology in Biomedicine, vol. 14, No. 3, May 2010, pp. 776-785, 10 pages.

Kumar, M., et al., "Distance PPG: Robust non-contact vital signs monitoring using a camera", Biomedical Optics Express, vol. 6, No. 5, May 1, 2015, 24 pages.

Kwon, Sungjun, et al., "Validation of heart rate extraction using video imaging on a built-in camera system of a smartphone", 34th Annual International Conference of the IEEE Embs, San Diego, CA, USA, Aug. 28-Sep. 1, 2012, pp. 2174-2177, 4 pages.

Lai, C.J., et al., "Heated humidified high-flow nasal oxygen prevents intraoperative body temperature decrease in non-intubated thoracoscopy", Journal of Anesthesia, Oct. 15, 2018, 8 pages.

Li , et al., "A Non-Contact Vision-Based System for Respiratory Rate Estimation", IEEE 978-1-4244-7929-0/14, 2014, pp. 2119-2122, 4 pages.

Sokooti, Hess , et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.

Rezaei, Mahdi , et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.

Sathyamoorthy, Adarsh Jagan, et al., "COVID-Robot: Monitoring Social Distancing Constraints in Crowded Scenarios", Aug. 21, 2020, pp. 1-11, 11 pages.

Liu, X., et al., "An Image Captioning Method for Infant Sleeping Environment Diagnosis", Springer International Publishing, May 15, 2019, pp. 18-26, 9 pages.

(56) References Cited

OTHER PUBLICATIONS

Al-Naji, Ali, et al., "Real Time Apnoea Monitoring of Children Using the Microsoft Kinect Sensor: A Pilot Study", Sensors, 17(286), Feb. 3, 2017, 15 pages.

Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.

Bartula, M., et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.

Reyes, B.A., et al., "Tidal vol. and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.

Transue, S., et al., "Real-time Tidal vol. Estimation using Iso-surface Reconstruction", 2016 IEEE First International Conference on Connected Health: Applications, Systems and Engineering Technologies (CHASE), Jun. 27, 2016, pp. 209-218, 10 pages.

Yu, M.C., et al., "Noncontact Respiratory Measurement of Volume Change Using Depth Camera", 2012 Annual International Conference of the IEEE Engeineering in Medicine and Biology Society, Aug. 28, 2012, pp. 2371-2374, 4 pages.

\* cited by examiner

SYSTEMS AND METHODS FOR NON-CONTACT RESPIRATORY MONITORING

CROSS-REFERENCE TO RELATED APPLICATIONS

The present application claims priority under 35 U.S.C. § 119(e) to U.S. Provisional Patent Application No. 63/142,298, entitled "Systems and Methods for Non-Contact Respiratory Monitoring", filed Jan. 27, 2021, the entirety of which is incorporated herein by reference.

BACKGROUND

Many conventional medical monitors require attachment of a sensor to a patient in order to detect physiologic signals from the patient and transmit detected signals through a cable to the monitor. These monitors process the received signals and determine vital signs such as the patient's pulse rate, respiration rate, and arterial oxygen saturation. For example, a pulse oximeter is a finger sensor that may include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a new field of patient monitoring that uses a remote video camera to detect physical attributes of the patient. This type of monitoring may also be called "non-contact" monitoring in reference to the remote video sensor, which does not contact the patient.

SUMMARY

The present disclosure is directed to methods and systems for non-contact monitoring of a patient to determine respiratory parameters such as respiration rate, tidal volume, minute volume, oxygen saturation, and other parameters such as motion and activity. The systems and methods utilize a first, video signal received from the patient and from that extract a distance or depth signal from the relevant area to calculate the parameter(s) from the depth signal. The systems and methods also receive a second, light intensity signal, such as from an IR feature projected onto the patient, and from that calculate the parameter(s) from the light intensity signal. The parameter(s) from the two signals can be combined or compared to provide a qualified output parameter.

One particular embodiment described herein is a method qualifying a respiratory parameter of a patient by combining two measurements or calculations of that parameter. The method includes determining the respiratory parameter of the patient using depth information determined by a non-contact patient monitoring system in a region of interest (ROI), over time, between the patient and the monitoring system. The method also includes determining the respiratory parameter of the patient using light intensity information in the ROI, over time, from the patient, which is done by: projecting a feature onto the patient in the ROI; measuring a first reflected light intensity from the feature at a first time; measuring a second reflected light intensity from the feature at a second time subsequent to the first time; and comparing the first reflected light intensity and the second reflected light intensity to determine a change in position or location of the feature over time. The two parameters, the respiratory parameter of the patient using depth information and the respiratory parameter of the patient using light intensity information, are combined to provide or qualify a combined respiratory parameter.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other embodiments are also described and recited herein.

DETAILED DESCRIPTION

Figure 1:
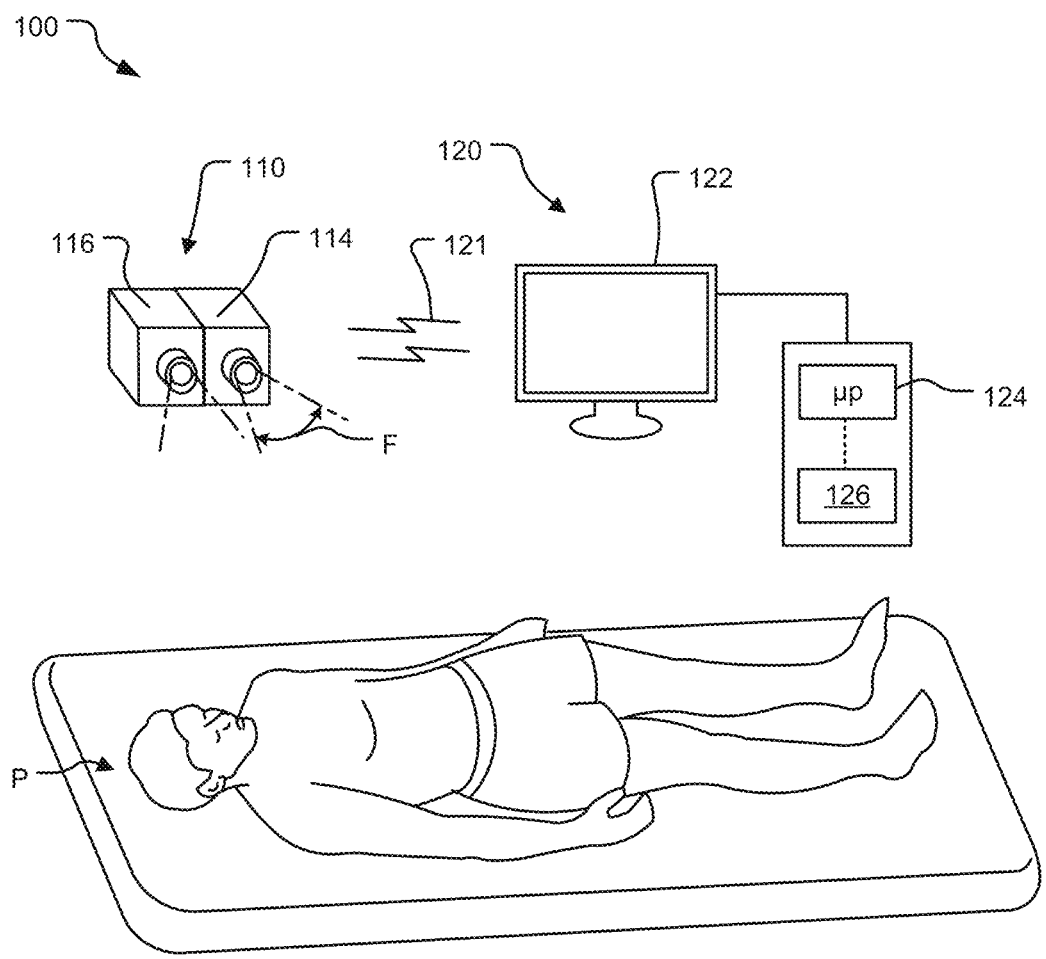
FIG. 1 is a schematic diagram of an example non-contact patient monitoring system according to various embodiments described herein.

As described above, the present disclosure is directed to medical monitoring, and in particular, non-contact, video-based monitoring of respiratory parameters, including respiration rate, tidal volume, minute volume, oxygen saturation, and other parameters such as motion or activity. Systems and methods are described for receiving a video signal view of a patient, identifying a physiologically relevant area within the video image (such as a patient's forehead or chest), extracting a distance or depth signal from the relevant area and also a light intensity signal from the relevant area, filtering those signals to focus on a physiologic component, calculating a vital sign from the signals, measuring the vital sign from the signals, and comparing the calculated vital sign to the measured vital sign.

The signals are detected by a camera or camera system that views but does not contact the patient. With appropriate selection and filtering of the signals detected by the camera, the physiologic contribution by the detected depth signal can be isolated and measured. Additionally, the light intensity signal is detected by at least one camera that views but does not contact the patient. With appropriate selection and filtering of the signal detected, the physiologic contribution can be estimated or calculated.

This approach has the potential to improve patient mobility and comfort, along with many other potential advantages discussed below.

Remote sensing of a patient with video-based monitoring systems presents several challenges. One challenge is due to motion or movement of the patient. The problem can be illustrated with the example of conventional, contact, pulse oximetry, which utilizes a sensor including two light emitters and a photodetector. The sensor is placed in contact with the patient, such as by clipping or adhering the sensor around a finger, toe, or ear of the patient. The sensor's emitters emit light of two particular wavelengths into the patient's tissue, and the photodetector detects the light after it is reflected or transmitted through the tissue. The detected light signal, called a photoplethysmogram (PPG), modulates with the patient's heartbeat, as each arterial pulse passes through the monitored tissue and affects the amount of light absorbed or scattered. Movement of the patient can interfere with this contact-based oximetry, introducing noise into the PPG signal due to compression of the monitored tissue, disrupted coupling of the sensor to the finger, pooling or movement of blood, exposure to ambient light, and other factors. Modern pulse oximeters use filtering algorithms to remove noise introduced by motion and to continue to monitor the pulsatile arterial signal.

However, movement in non-contact pulse oximetry creates different complications, due to the extent of movement possible between the patient and the camera. Because the camera is remote from the patient, the patient may move toward or away from the camera, creating a moving frame of reference, or may rotate with respect to the camera, effectively morphing the region that is being monitored. Thus, the monitored tissue can change morphology within the image frame over time. This freedom of motion of the monitored tissue with respect to the detector introduces new types of motion noise into the video-based signals.

Another challenge is ambient light. In this context, "ambient light" means surrounding light not emitted by components of the camera or the monitoring system. In contact-based pulse oximetry, the desired light signal is the reflected and/or transmitted light from the light emitters on the sensor, and ambient light is entirely noise. The ambient light can be filtered, removed, or avoided in order to focus on the desired signal. In contact-based pulse oximetry, contact-based sensors can be mechanically shielded from ambient light, and direct contact between the sensor and the patient also blocks much of the ambient light from reaching the detector. By contrast, in non-contact pulse oximetry, the desired physiologic signal is generated or carried by the ambient light source; thus, the ambient light cannot be entirely filtered, removed, or avoided as noise. Changes in lighting within the room, including overhead lighting, sunlight, television screens, variations in reflected light, and passing shadows from moving objects all contribute to the light signal that reaches the camera. Even subtle motions outside the field of view of the camera can reflect light onto the patient being monitored.

Non-contact monitoring such as video-based monitoring can deliver significant benefits over contact monitoring if the above-discussed challenges can be addressed. Some video-based monitoring can reduce cost and waste by reducing use of disposable contact sensors, replacing them with reusable camera systems. Video monitoring may also reduce the spread of infection, by reducing physical contact between caregivers and patients. Video cameras can improve patient mobility and comfort, by freeing patients from wired tethers or bulky wearable sensors. In some cases, these systems can also save time for caregivers, who no longer need to reposition, clean, inspect, or replace contact sensors.

The present disclosure describes methods and systems for non-contact monitoring of a patient to determine respiratory parameters such as respiration rate, tidal volume, minute volume, oxygen saturation, and other parameters such as motion and activity. The systems and methods receive a first, video signal from the patient and from that extract a distance or depth signal from the relevant area to calculate the parameter(s) from the depth signal. The systems and methods also receive a second signal, a light intensity signal reflected from the patient, and from that calculate the parameter(s) from the light intensity signal. The parameter(s) from the two signals can be combined or compared to provide a qualified output parameter. In some embodiments, the light intensity signal is a reflection of an IR feature projected onto the patient, such as by a projector.

The depth sensing feature of the system provides a measurement of the distance or depth between the detection system and the patient. One or two video cameras may be used to determine the depth, and change in depth, from the system to the patient. When two cameras, set at a fixed distance apart, are used, they offer stereo vision due to the slightly different perspectives of the scene from which distance information is extracted. When distinct features are present in the scene, the stereo image algorithm can find the locations of the same features in the two image streams. However, if an object is featureless (e.g., a smooth surface with a monochromatic color), then the depth camera system has difficulty resolving the perspective differences. By including an image projector to project features (e.g., in the form of dots, pixels, etc.) onto the scene, this projected feature can be monitored over time to produce an estimate of changing distance or depth.

In the following description, reference is made to the accompanying drawing that forms a part hereof and in which is shown by way of illustration at least one specific embodiment. The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

FIG. 1 shows a non-contact patient monitoring system 100 and a patient P according to an embodiment of the invention. The system 100 includes a non-contact detector system 110 placed remote from the patient P. In this embodiment, the detector system 110 includes a camera system 114, particularly, a camera that includes an infrared (IR) detection feature. The camera 114 may be a depth sensing camera, such as a Kinect camera from Microsoft Corp. (Redmond, Washington) or a RealSense™ D415, D435 or D455 camera from Intel Corp. (Santa Clara, California). The camera system 114 is remote from the patient P, in that it is spaced apart from and does not physically contact the patient P. The camera system 114 includes a detector exposed to a field of view F that encompasses at least a portion of the patient P.

The camera system 114 includes a depth sensing camera that can detect a distance between the camera system 114 and objects in its field of view F. Such information can be used, as disclosed herein, to determine that a patient is within the field of view of the camera system 114 and determine a region of interest (ROI) to monitor on the patient. Once an ROI is identified, that ROI can be monitored over time, and the change in depth of points within the ROI can represent movements of the patient associated with, e.g., breathing. Accordingly, those movements, or changes of depth points within the ROI, can be used to determine, e.g., respiration rate, tidal volume, minute volume, effort to breathe, etc.

In some embodiments, the field of view F encompasses exposed skin of the patient. In other embodiments, the field of view F encompasses a portion of the patient's torso, covered by a blanket, sheet, or gown.

The camera system 114 operates at a frame rate, which is the number of image frames taken per second (or other time period). Example frame rates include 20, 30, 40, 50, or 60 frames per second, greater than 60 frames per second, or other values between those. Frame rates of 20-30 frames per second produce useful signals, though frame rates above 100 or 120 frames per second are helpful in avoiding aliasing with light flicker (for artificial lights having frequencies around 50 or 60 Hz).

The distance from the ROI on the patient P to the camera system 114 is measured by the system 100. Generally, the camera system 114 detects a distance between the camera system 114 and the surface within the ROI; the change in depth or distance of the ROI can represent movements of the patient, e.g., associated with breathing.

In some embodiments, the system 100 determines a skeleton outline of the patient P to identify a point or points from which to extrapolate the ROI. For example, a skeleton may be used to find a center point of a chest, shoulder points, waist points, and/or any other points on a body. These points can be used to determine the ROI. For example, the ROI may be defined by filling in the area around a center point of the chest. Certain determined points may define an outer edge of an ROI, such as shoulder points. In other embodiments, instead of using a skeleton, other points are used to establish an ROI. For example, a face may be recognized, and a chest area inferred in proportion and spatial relation to the face. In other embodiments, the system 100 may establish the ROI around a point based on which parts are within a certain depth range of the point. In other words, once a point is determined that an ROI should be developed from, the system can utilize the depth information from the depth sensing camera system 114 to fill out the ROI as disclosed herein. For example, if a point on the chest is selected, depth information is utilized to determine the ROI area around the determined point that is a similar distance from the depth sensing camera 114 as the determined point. This area is likely to be a chest.

In another example, the patient P may wear a specially configured piece of clothing that identifies points on the body such as shoulders or the center of the chest. The system 100 may identify those points by identifying the indicating feature of the clothing. Such identifying features could be a visually encoded message (e.g., bar code, QR code, etc.), or a brightly colored shape that contrasts with the rest of the patient's clothing, etc. In some embodiments, a piece of clothing worn by the patient may have a grid or other identifiable pattern on it to aid in recognition of the patient and/or their movement. In some embodiments, the identifying feature may be stuck on the clothing using a fastening mechanism such as adhesive, a pin, etc. For example, a small sticker or other indicator may be placed on a patient's shoulders and/or center of the chest that can be easily identified from an image captured by a camera. In some embodiments, the indicator may be a sensor that can transmit a light or other information to the camera system 114 that enables its location to be identified in an image so as to help define the ROI. Therefore, different methods can be used to identify the patient and define an ROI.

The ROI size may differ according to the distance of the patient from the camera system. The ROI dimensions may vary linearly with the distance of the patient from the camera system. This ensures that the ROI scales according with the patient and covers the same part of the patient regardless of the patient's distance from the camera. This is accomplished by applying a scaling factor that is dependent on the distance of the patient (and the ROI) from the camera. In order to properly measure the depth changes, the actual size (area) of the ROI is determined and movements of that ROI are measured. The measured movements of the ROI and the actual size of the ROI are then used to calculate the respiratory parameter, e.g., a tidal volume. Because a patient's distance from a camera can change, e.g., due to rolling or position readjustment, the ROI associated with that patient can appear to change in size in an image from a camera. However, using the depth sensing information captured by a depth sensing camera or other type of depth sensor, the system can determine how far away from the camera the patient (and their ROI) actually is. With this information, the actual size of the ROI can be determined, allowing for accurate measurements of depth change regardless of the distance of the camera to the patient.

In some embodiments, the system 100 may receive a user input to identify a starting point for defining an ROI. For example, an image may be reproduced on an interface, allowing a user of the interface to select a patient for monitoring (which may be helpful where multiple humans are in view of a camera) and/or allowing the user to select a point on the patient from which the ROI can be determined (such as a point on the chest). Other methods for identifying a patient, points on the patient, and defining an ROI may also be used.

However, if the ROI is essentially featureless (e.g., a smooth surface with a monochromatic color, such as a blanket or sheet covering the patient P), then the camera system 114 may have difficulty resolving the perspective differences. To address this, the system 100 includes a projector 116 to project individual features (e.g., dots, crosses or Xs, lines, individual pixels, etc.) onto the ROI; the features may be visible light, UV light, infrared (IR) light, etc. The projector may be part of the detector system 110 or the overall system 100.

The projector 116 generates a sequence of features over time on the ROI from which is monitored and measured the reflected light intensity. A measure of the amount, color, or brightness of light within all or a portion of the reflected feature over time is referred to as a light intensity signal. The camera system 114 detects the features from which this light intensity signal is determined. In an embodiment, each visible image projected by the projector 116 includes a two-dimensional array or grid of pixels, and each pixel may include three color components—for example, red, green, and blue. A measure of one or more color components of one or more pixels over time is referred to as a "pixel signal," which is a type of light intensity signal. In another embodiment, when the projector 116 projects an IR feature, which is not visible to a human eye, the camera system 114 includes an infrared (IR) sensing feature. In another embodiment, the projector 116 projects a UV feature. In yet other embodiments, other modalities including millimeter-wave, hyper-spectral, etc., may be used.

The projector 116 may alternatively or additionally project a featureless intensity pattern (e.g., a homogeneous, a gradient or any other pattern that does not necessarily have distinct features). In some embodiments, the projector 116, or more than one projector, can project a combination of a feature-rich pattern and featureless patterns on to the ROI.

For one projector 116 or multiple projectors, the emission power may be dynamically controlled to modulate the light emissions, in a manner as commonly done for pulse-oximeters with LED light.

The detected images and diffusion measurements are sent to a computing device 120 through a wired or wireless connection 121. The computing device 120 includes a display 122, a processor 124, and hardware memory 126 for storing software and computer instructions. Sequential image frames of the patient P are recorded by the video camera system 114 and sent to the processor 124 for analysis. The display 122 may be remote from the camera system 114, such as a video screen positioned separately from the processor and memory. Other embodiments of the computing device 120 may have different, fewer, or additional components than shown in FIG. 1. In some embodiments, the computing device may be a server. In other embodiments, the computing device of FIG. 1 may be additionally connected to a server. The captured images (e.g., still images, or video) can be processed or analyzed at the computing device and/or at the server to determine the parameters of the patient P as disclosed herein.

Figure 2:
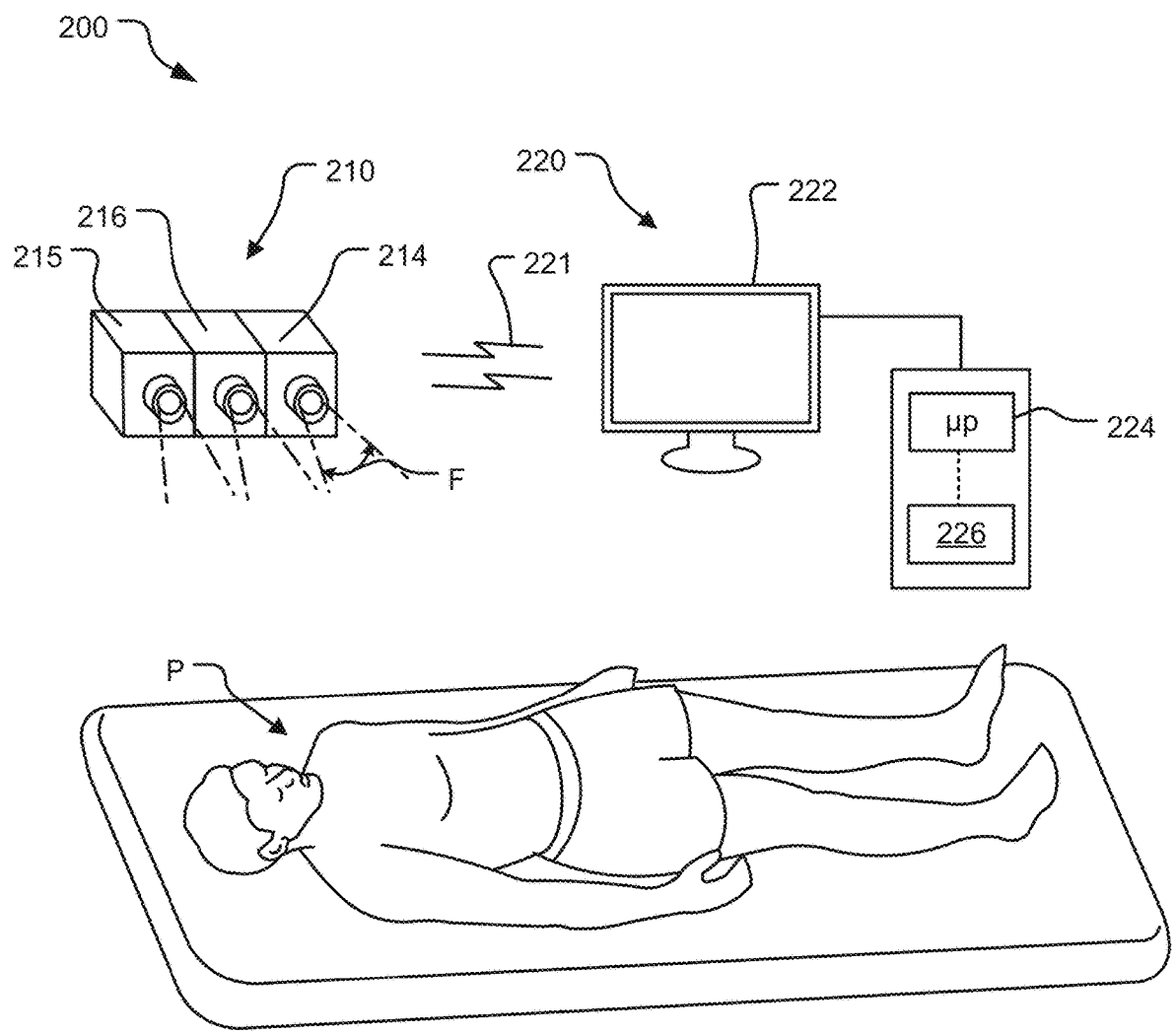
FIG. 2 is a schematic diagram of another example non-contact patient monitoring system according to various embodiments described herein.

FIG. 2 shows another non-contact patient monitoring system 200 and a patient P. The system 200 includes a non-contact detector 210 placed remote from the patient P. In this embodiment, the detector 210 includes a first camera 214 and a second camera 215, at least one of which includes an infrared (IR) camera feature. The cameras 214, 215 are positioned so that their ROI at least intersect, in some embodiments overlap. The detector 210 also includes an IR projector 216, which projects individual features (e.g., dots, crosses or Xs, lines, or a featureless pattern, or a combination thereof etc.) onto the ROI. The projector 216 can be separate from the detector 210 or integral with the detector 210, as shown in FIG. 2. In some embodiments, more than one projector 216 can be used. Both cameras 214, 215 are aimed to have the features projected by the projector 216 to be in the ROI. The cameras 214, 215 and projector 216 are remote from the patient P, in that they are spaced apart from and do not contact the patient P. In this implementation, the projector 216 is physically positioned between the cameras 214, 215, whereas in other embodiments it may not be so.

The distance from the ROI to the cameras 214, 215 is measured by the system 200. Generally, the cameras 214, 215 detect a distance between the cameras 214, 215 and the projected features on a surface within the ROI. The light from the projector 216 hitting the surface is scattered/diffused in all directions; the diffusion pattern depends on the reflective and scattering properties of the surface. The cameras 214, 215 also detect the light intensity of the projected individual features in their ROIs. From the distance and the light intensity, at least one physiological parameter of the patient P is monitored.

Figure 3A:
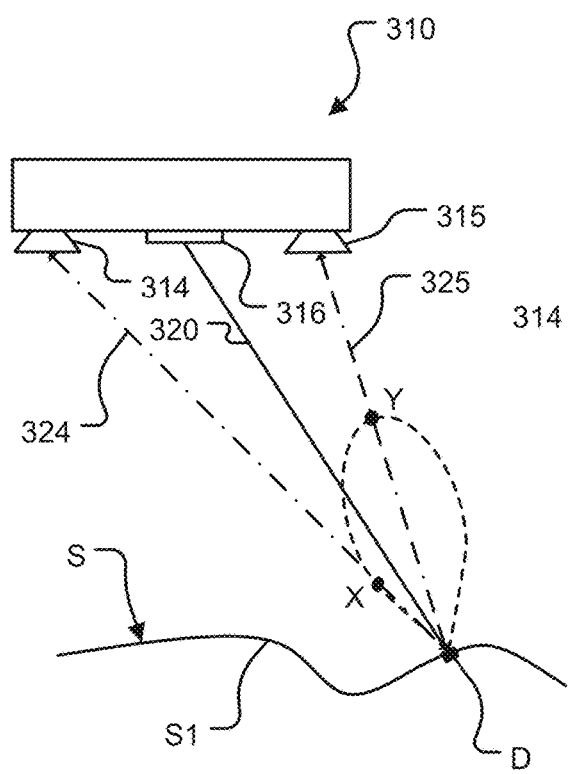
FIG. 3A and FIG. 3B are schematic diagrams showing two embodiments using the example non-contact patient monitoring system of FIG. 2.
Figure 3B:
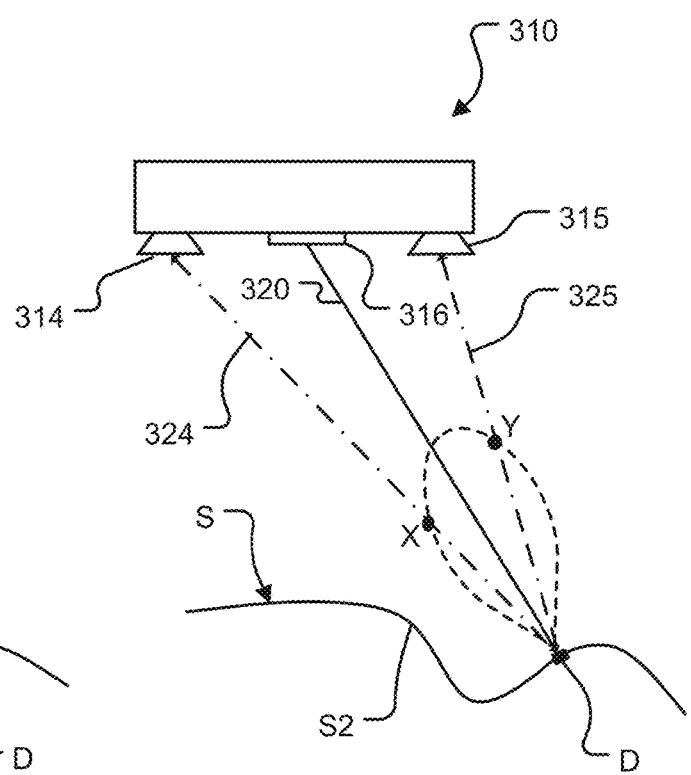

FIG. 3A and FIG. 3B both show a non-contact detector 310 having a first camera including an IR detection feature 314, a second IR camera including an IR detection feature 315, and an IR projector 316. A dot D is projected by the projector 316 onto a surface S, e.g., of a patient, via a beam 320. Light from the dot D is reflected by the surface S and is detected by the camera 314 as beam 324 and by the camera 315 as beam 325.

The light intensity returned to and observed by the cameras 314, 315 depends on the diffusion pattern caused by the surface S (e.g., the surface of a patient), the distance between the cameras 314, 315 and surface S, the surface gradient, and the orientation of the cameras 314, 315 relative to the surface S. In FIG. 3A, the surface S has a first profile S1 and in FIG. 3B, the surface S has a second profile S2 different than S1; as an example, the first profile S1 is during an exhale breath of a patient and the second profile S2 is during an inhale breath of the patient. Because the surface profiles S1 and S2 differ, the deflection pattern from the dot D on each of the surfaces differs for the two figures.

During breathing (respiration), the light intensity reflection off the dot D observed by the cameras 314, 315 changes because the surface profile S1 and S2 (specifically, the gradient) changes as well as the distance between the surface S and the cameras 314, 315. FIG. 3A shows the surface S having the surface profile S1 at time instant $t=t_n$ and FIG. 3B shows the surface S having the surface profile S2 at a later time, specifically $t=t_{n+1}$, with S2 being slightly changed due to motion caused by respiration. Consequently, the intensity of the projected dot D observed by the cameras 314, 315 will changed due to the changes of the surface S. In FIG. 3A, a significantly greater intensity is measured by the camera 315 than the camera 314, seen by the x and y on the beams 324, 325, respectively. In FIG. 3B, y is less than y in FIG. 3A, whereas x in FIG. 3B is greater than x in FIG. 3A. The manner in how these intensities change depends on the diffusion pattern and its change over time. As seen in FIGS. 3A and 3B, the light intensities as measured by the cameras 314 and 315 have changed between FIGS. 3A and 3B, and hence, the surface S has moved. Each camera will generate a signal because of the change of the intensity of dot D when the surface profile changes from time instant $t=t_n$ to $t=t_{n+1}$ due to movement.

In some other embodiments, a single camera and light projector can be used. For example, in FIGS. 3A and 3B, the camera 315 is not present or is ignored. It is clear that the camera 314 will still produce a change in light intensity from time instant $t=t_n$ to $t=t_{n+1}$ due to movement. This embodiment will therefore produce only a single signal as opposed to the two signals generated by the embodiment discussed in the previous paragraph.

Figure 4:
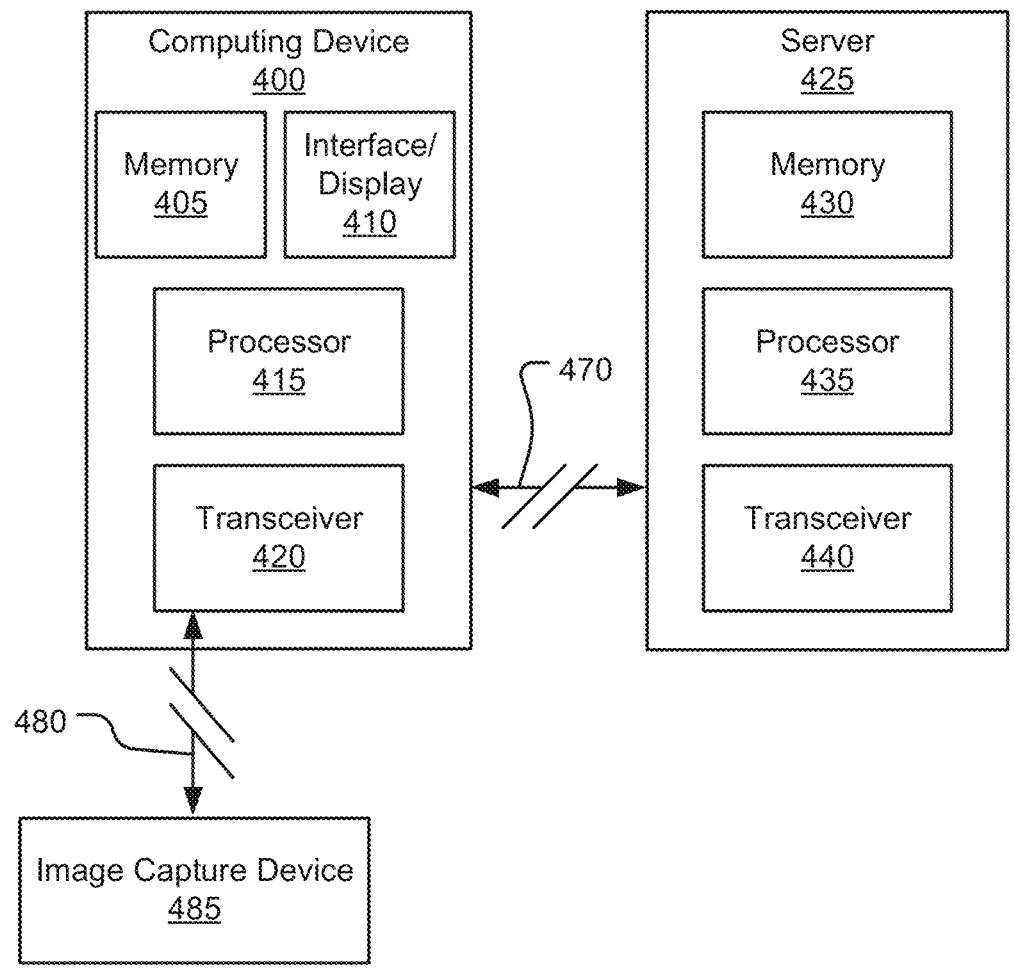
FIG. 4 is a block diagram of a computing device, a server, and an image capture device according to various embodiments described herein.

FIG. 4 is a block diagram illustrating a system including a computing device 400, a server 425, and an image capture device 485 (e.g., a camera, e.g., the camera system 114 or cameras 214, 215). In various embodiments, fewer, additional and/or different components may be used in the system.

The computing device 400 includes a processor 415 that is coupled to a memory 405. The processor 415 can store and recall data and applications in the memory 405, including applications that process information and send commands/signals according to any of the methods disclosed herein. The processor 415 may also display objects, applications, data, etc. on an interface/display 410. The processor 415 may also or alternatively receive inputs through the interface/ display 410. The processor 415 is also coupled to a transceiver 420. With this configuration, the processor 415, and subsequently the computing device 400, can communicate with other devices, such as the server 425 through a connection 470 and the image capture device 485 through a connection 480. For example, the computing device 400 may send to the server 425 information determined about a patient from images captured by the image capture device 485, such as depth information of a patient in an image.

The server 425 also includes a processor 435 that is coupled to a memory 430 and to a transceiver 440. The processor 435 can store and recall data and applications in the memory 430. With this configuration, the processor 435, and subsequently the server 425, can communicate with other devices, such as the computing device 400 through the connection 470.

The computing device 400 may be, e.g., the computing device 120 of FIG. 1 or the computing device 220 of FIG. 2. Accordingly, the computing device 400 may be located remotely from the image capture device 485, or it may be local and close to the image capture device 485 (e.g., in the same room). The processor 415 of the computing device 400 may perform any or all of the various steps disclosed herein. In other embodiments, the steps may be performed on a processor 435 of the server 425. In some embodiments, the various steps and methods disclosed herein may be performed by both of the processors 415 and 435. In some embodiments, certain steps may be performed by the processor 415 while others are performed by the processor 435. In some embodiments, information determined by the processor 415 may be sent to the server 425 for storage and/or further processing.

The devices shown in the illustrative embodiment may be utilized in various ways. For example, either or both of the connections 470, 480 may be varied. For example, either or both the connections 470, 480 may be a hard-wired connection. A hard-wired connection may involve connecting the devices through a USB (universal serial bus) port, serial port, parallel port, or other type of wired connection to facilitate the transfer of data and information between a processor of a device and a second processor of a second device. In another example, one or both of the connections 470, 480 may be a dock where one device may plug into another device. As another example, one or both of the connections 470, 480 may be a wireless connection. These connections may be any sort of wireless connection, including, but not limited to, Bluetooth connectivity, Wi-Fi connectivity, infrared, visible light, radio frequency (RF) signals, or other wireless protocols/methods. For example, other possible modes of wireless communication may include near-field communications, such as passive radio-frequency identification (RFID) and active RFID technologies. RFID and similar near-field communications may allow the various devices to communicate in short range when they are placed proximate to one another. In yet another example, the various devices may connect through an internet (or other network) connection. That is, one or both of the connections 470, 480 may represent several different computing devices and network components that allow the various devices to communicate through the internet, either through a hard-wired or wireless connection. One or both of the connections 470, 480 may also be a combination of several modes of connection.

The configuration of the devices in FIG. 4 is merely one physical system on which the disclosed embodiments may be executed. Other configurations of the devices shown may exist to practice the disclosed embodiments. Further, configurations of additional or fewer devices than the ones shown in FIG. 4 may exist to practice the disclosed embodiments. Additionally, the devices shown in FIG. 4 may be combined to allow for fewer devices than shown or separated such that more than the three devices exist in a system. It will be appreciated that many various combinations of computing devices may execute the methods and systems disclosed herein. Examples of such computing devices may include other types of medical devices and sensors, infrared cameras/detectors, night vision cameras/detectors, other types of cameras, radio frequency transmitters/receivers, smart phones, personal computers, servers, laptop computers, tablets, RFID enabled devices, or any combinations of such devices.

The method of this disclosure utilizes depth (distance) information between the camera(s) and the patient to determine a respiratory parameter such as respiratory rate. A depth image or depth map, which includes information about the distance from the camera to each point in the image, can be measured or otherwise captured by a depth sensing camera, such as a Kinect camera from Microsoft Corp. (Redmond, Washington) or a RealSense™ D415, D435 or D455 camera from Intel Corp. (Santa Clara, California) or other sensor devices based upon, for example, millimeter wave and acoustic principles to measure distance.

The depth image or map can be obtained by a stereo camera, a camera cluster, camera array, or a motion sensor focused on a ROI, such as a patient's chest. In some embodiments, the camera(s) are focused on visible or IR features in the ROI. Each projected feature may be monitored, less than all the features in the ROI may be monitored or all the pixels in the ROI can be monitored.

When multiple depth images are taken over time in a video stream, the video information includes the movement of the points within the image, as they move toward and away from the camera over time.

Because the image or map includes depth data from the depth sensing camera, information on the spatial location of the patient (e.g., the patient's chest) in the ROI can be determined. This information can be contained, e.g., within a matrix. As the patient breathes, the patient's chest moves toward and away from the camera, changing the depth information associated with the images over time. As a result, the location information associated with the ROI changes over time. The position of individual points within the ROI (i.e., the change in distance) may be integrated across the area of the ROI to provide a change in volume over time.

For example, movement of a patient's chest toward a camera as the patient's chest expands forward represents inhalation. Similarly, movement backward, away from the camera, occurs when the patient's chest contrasts with exhalation. This movement forward and backward can be tracked to determine a respiration rate.

Additionally, the changes in the parameter can be monitored over time for anomalies, e.g., signals of sleep apnea or other respiratory patterns.

In some embodiments, the depth signal from the non-contact system may need to be calibrated, e.g., to provide an absolute measure of volume. For example, the volume signal obtained from integrating points in a ROI over time may accurately track a patient's tidal volume and may be adjusted by a calibration factor or factors. The calibration or correction factor could be a linear relationship such as a linear slope and intercept, a coefficient, or other relationships. As an example, the volume signal obtained from a video camera may under-estimate the total tidal volume of a patient, due to underestimating the volume of breath that expands a patient's chest backward, away from the camera, which is not measured by the depth cameras, or upward orthogonal to the line of sight of the camera. Thus, the non-contact volume signal may be adjusted by simply adding or applying a correction or calibration factor. This correction factor can be determined in a few different ways, including measuring the actual parameter to obtain a reference value to use as a baseline.

In some embodiments, demographic data about a patient may be used to calibrate the depth or volume signal. From a knowledge of the patient's demographic data, which may include height, weight, chest circumference, BMI, age, sex, etc., a mapping from the measured volume signal to an actual volume signal may be determined. For example, patients of smaller height and/or weight may have less of a weighting coefficient for adjusting measured volume for a given ROI box size than patients of greater height and/or weight. Different corrections or mappings may also be used for other factors, such as whether the patient is under bedding, type/style of clothing worn by a patient (e.g., t-shirt, sweatshirt, hospital gown, dress, v-neck shirt/dress, etc.), thickness/material of clothing/bedding, a posture of the patient, and/or an activity of the patient (e.g., eating, talking, sleeping, awake, moving, walking, running, etc.).

As indicated above, in addition to the methodology of this disclosure utilizing depth (distance) information between the camera(s) and the patient to determine a respiratory parameter, the method also uses reflected light intensity from projected IR features (e.g., dots, grid, stripes, crosses, squares, etc., or a featureless pattern, or a combination thereof) in the scene to estimate the depth (distance).

Figure 5A:
FIG. 5A is a photograph of a patient being monitored by a non-contact patient monitoring system according to various embodiments described herein, with a region of interest delineated.
Figure 5B:
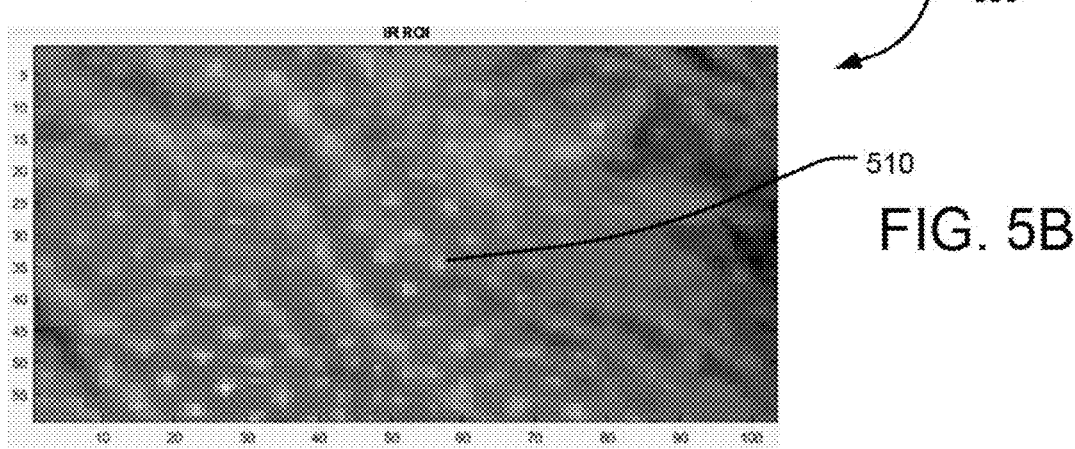
FIG. 5B is an enlarged portion of the region of interest of FIG. 5A.

FIG. 5A shows an IR image from a subject patient. A region of interest (ROI) 500 is indicated on the image by the boxed (rectangular) region, although the ROI could have other, e.g., non-rectangular, shapes. The ROI 500 is shown enlarged in FIG. 5B with a pattern of projected IR features 510 readily visible in the figure. It can be readily seen that the features 510 have a varying intensity across the ROI 500. In addition, the intensity of the features 510 varies over time as the ROI 500 moves, e.g., during a respiratory cycle.

This change of intensity over time of each of the projected features is used to produce a respiratory waveform plot. The waveform is formed by aggregating all the pixel values, at an instant in time, over time, from across the ROI 500 to generate a pattern signal shown in FIG. 5C. In some embodiments, less than all the projected features in the ROI 500 are monitored; for example, only a random sampling of the projected features is monitored, or for example, every third feature is monitored. In some embodiments, each feature reflection over time is monitored only for a predetermined duration, to determine which projected features provide an accurate or otherwise desired light intensity signal, and then those selected features are monitored to obtain the signal. In some embodiments, each pixel in the ROI is monitored and the light intensity signal obtained.

Figure 5C:
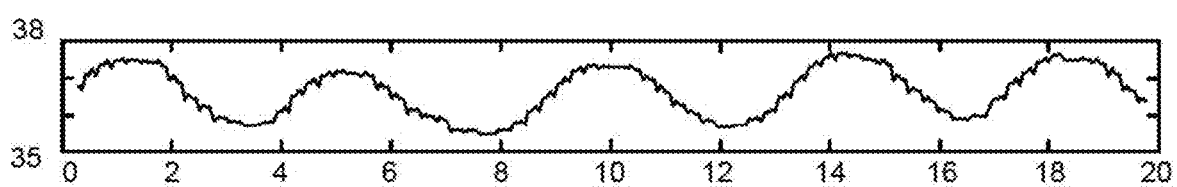
FIG. 5C is a graphical representation of data from a non-contact patient monitoring system according to various embodiments described herein.
Figure 5D:
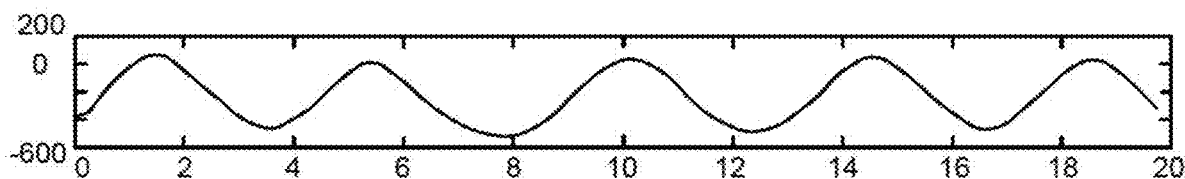
FIG. 5D is a graphical representation of additional data from a non-contact patient monitoring system according to various embodiments described herein.

The respiratory modulations over time, extracted from the varying intensity of the projected features, closely match those obtained from the respiration depth (distance) measured by the depth camera(s) (shown in FIG. 5D).

It should be noted that the phase of the intensity pattern signal (FIG. 5D) may be 180 degrees out of phase with that of the respiration modulation signal (FIG. 5C). This would be due the direction of the movement of the surface (e.g., exhale versus inhale) and gradient of the surface as well as orientation of the camera(s) relative to the surface, all which play a role in modulating the reflected light.

Across the whole ROI 500, some features (e.g., dots or each pixel) may produce "in phase" modulations and some may be "out of phase." These may be combined separately to produce two signals. Light returning from each of these features may be combined to produce a single respiratory signal, for example by inverting or phase-shifting by 180 degrees so where necessary to produce all in phase and then combining to get a combined pattern signal.

This method for producing a respiratory signal, i.e., from the intensity of the light diffusion, is independent from the depth data used to produce a signal representative of the respiratory parameter. This secondary pattern signal, from the light intensity, can be used to enhance or confirm the measurement of the respiratory parameters from the depth data.

Figure 6:
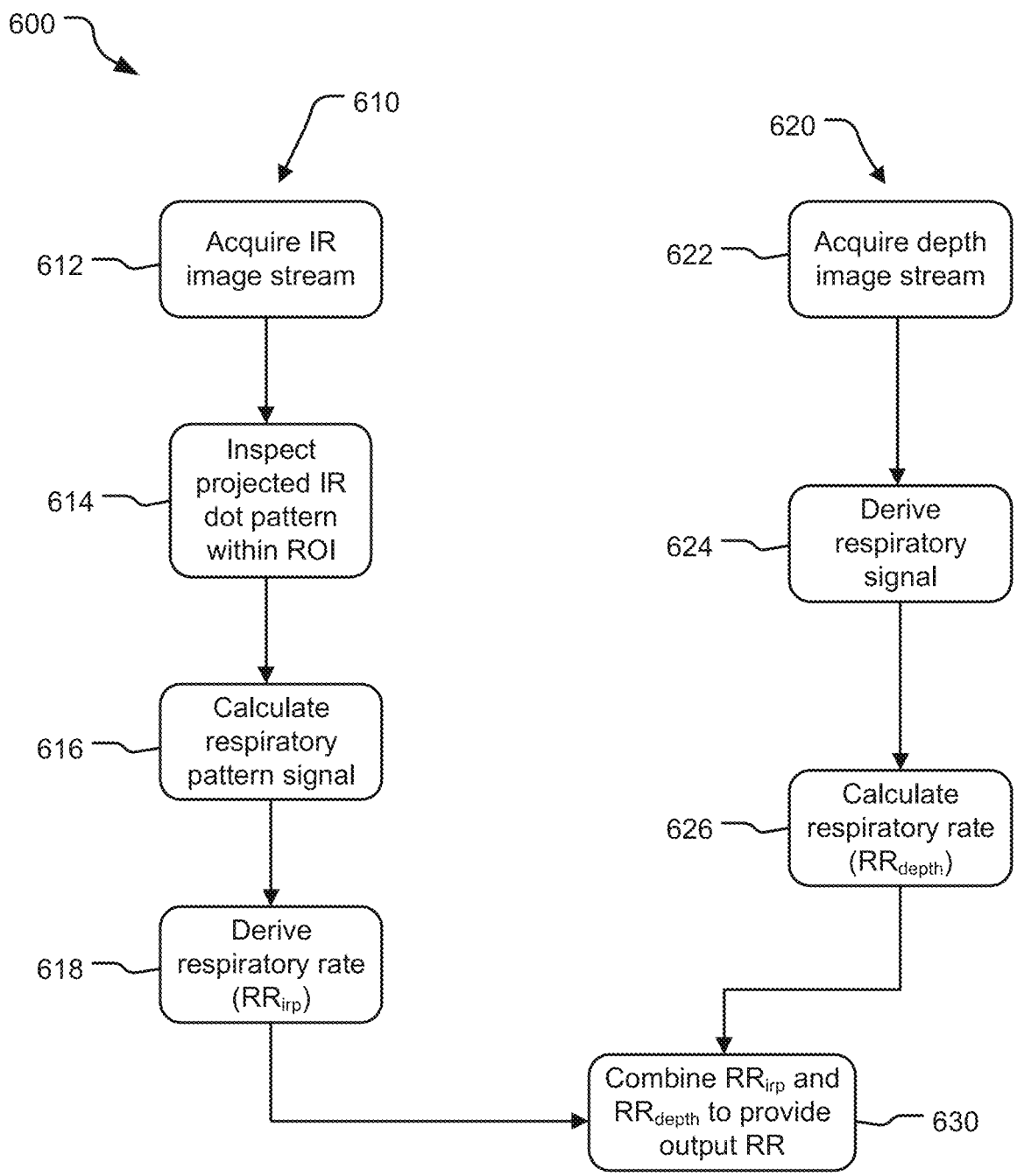
FIG. 6 is a stepwise method of an example method of using a non-contact patient monitoring system according to various embodiments described herein.

For example, the calculation of respiratory rate (determined from, e.g., a plot such as FIG. 5C) can be combined with a similar plot of the respiratory rate obtained from the depth camera ($RR_{depth}$). This may be done, e.g., by computing respiratory rate from each signal and then averaging the two numbers, or, with a more advanced method, such as Kalman filtering. FIG. 6 shows a method 600 for combining the data from the depth measurements with the data from the light intensity measurements to provide a combined parameter. In FIG. 6, the method 600 is particularly directed to respiratory rate, whereas in other embodiments a similar method is used to provide a different respiratory parameter.

The method 600 includes a first branch 610 that derives a respiratory parameter (specifically for this example, the respiratory rate ($RR_{irp}$)) from the light intensity measurements and a second branch 620 that calculates the respiratory parameter (specifically for this example, the respiratory rate ($RR_{depth}$)) from the depth measurements. The method 600 combines the derived respiratory rate ($RR_{irp}$) from the first branch 610 with the calculated respiratory rate ($RR_{depth}$) from the second branch 620.

For the respiratory rate ($RR_{irp}$) derived from the light intensity measurements, the method 600 includes a step 612 where the IR images are acquired of the surface being monitored. The features within the desired ROI are inspected in step 614 for their light intensity and change in light intensity over time. From the intensity information obtained in step 614, a respiratory pattern signal is calculated in step 616. From this patterned signal, the respiratory rate ($RR_{irp}$) is derived.

For the respiratory rate ($RR_{depth}$) derived from the depth measurements, the method 600 includes step 622 where the depth image stream of the surface is acquired from a depth camera. A respiratory signal (e.g., volume) is derived from the depth stream in step 624, from which a respiratory rate ($RR_{depth}$) is calculated in step 626.

In step 630, the derived respiratory rate ($RR_{irp}$) from step 618 is combined with the respiratory rate ($RR_{depth}$) calculated in step 626. The two rates may be averaged (e.g., simple average or mean, median, etc.), added, or combined in any other manner. Either individual patterns or the combined pattern can be inspected for anomalies, e.g., signals of sleep apnea or other respiratory patterns.

Figure 7:
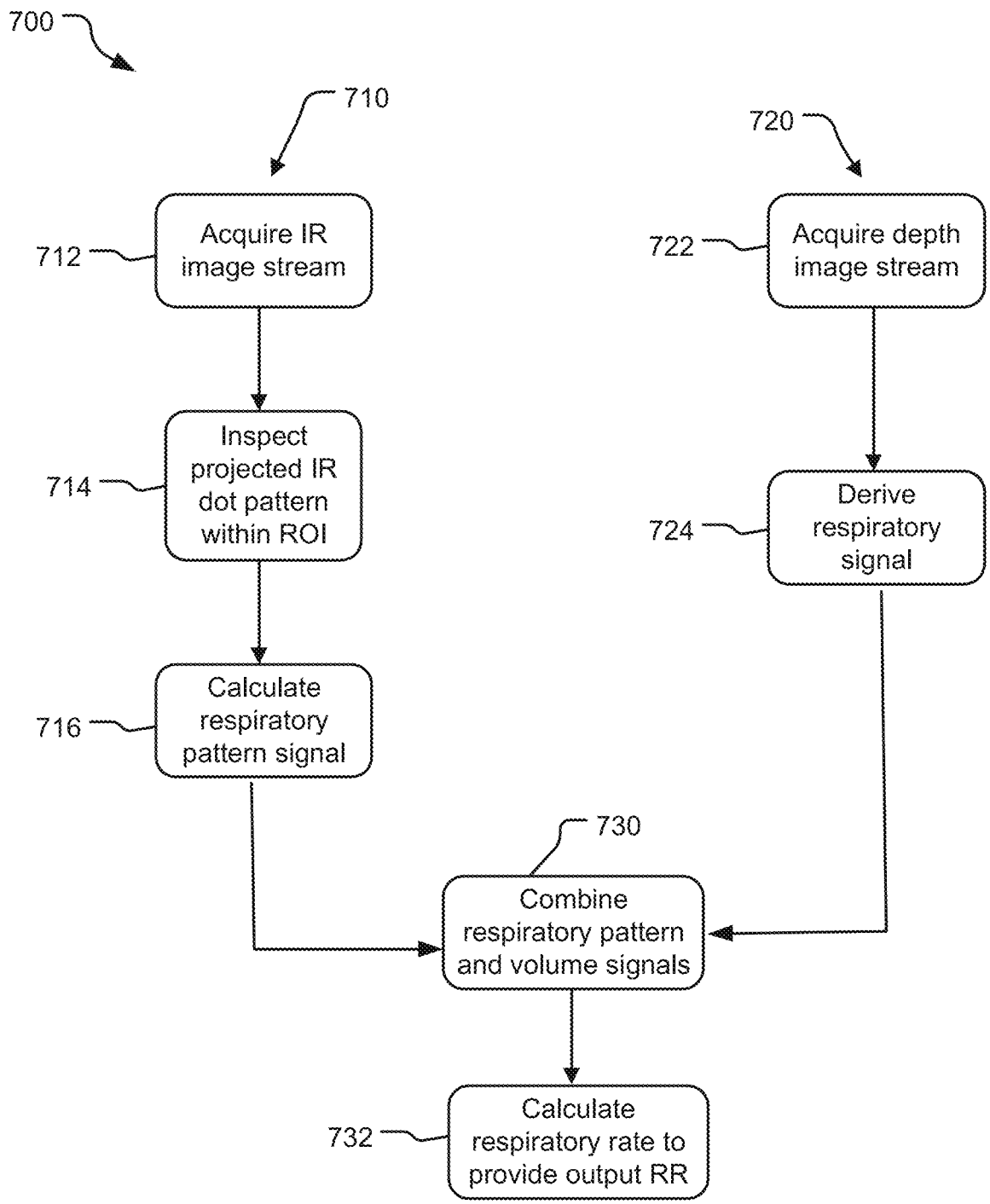
FIG. 7 is a stepwise method of another example method of using a non-contact patient monitoring system according to various embodiments described herein.

FIG. 7 shows another method 700 for combining the data from the depth measurements with the data from the light intensity measurements to provide a combined parameter; the method 700 is also directed to respiratory rate.

The method 700 includes a first branch 710 that derives a respiratory pattern from the light intensity measurements and a second branch 720 that calculates the respiratory parameter from the depth measurements. The method 700 combines the calculated respiratory pattern from the first branch 710 with the calculated respiratory signal from the second branch 720.

The method 700 includes a step 712 where the IR images are acquired of the surface being monitored. The features (e.g., dots) within the desired ROI are inspected in step 714 for their light intensity and change in light intensity over time. From the intensity information obtained in step 714, a respiratory pattern signal is calculated in step 716.

For the respiratory signal derived from the depth measurements, the method 700 includes step 722 where the depth image stream of the surface is acquired from a depth camera. A respiratory signal (e.g., respiratory volume) is derived from the depth stream in step 724.

The calculated respiratory pattern signal (from step 716) and the derived respiratory signal (from step 724) are combined in step 730, prior to calculating the respiration rate. The signals can be added, average, or otherwise combined in step 730 and then used to calculate a respiration rate in step 732 from the combined signal of step 730.

In both the method 600 of FIG. 6 and the method 700 of FIG. 7, the respiratory signal from the depth stream is combined with one respiratory signal obtained from the light intensity. In other embodiments, multiple light intensity signals may be obtained, e.g., one from IR features, one from visible features, one from UV features, etc., so that the respiratory signal from the depth stream is combined with multiple respiratory signals from multiple light intensity measurements.

Returning to and with respect to FIG. 2 and FIGS. 3A and 3B above, it is described that a system 200 with two cameras 214, 215 or a system 300 with two cameras 314, 315 can be used, the two cameras 214, 215 and 314, 315 providing a stereo property for one or both of the depth signal and the light intensity signal. When two cameras are used, although both cameras will produce very similar results, they each have their own noise characteristics. The noise, which is added to the respiratory signal, is generally uncorrelated and the overall noise component is therefore reduced by combining the results of two cameras. Thus, each camera produces a respiratory pattern and the results may then be, for example, averaged. Note that more than two cameras may be used to further improve the performance. Additionally, e.g., other, more advanced, methods for combining/fusing the different respiratory signals may be used including Kalman and particle filtering.

Thus, described herein are methods and systems for non-contact monitoring of a patient to determine respiratory parameters by utilizing a distance or depth signal from the patient to the system to calculate the parameter(s) from the depth signal and by utilizing a reflected light intensity signal from projected IR features to derive the same parameter(s). The parameter(s) from the two signals are combined or compared to provide an output parameter value or signal.

The above specification and examples provide a complete description of the structure and use of exemplary embodiments of the invention. The above description provides specific embodiments. It is to be understood that other embodiments are contemplated and may be made without departing from the scope or spirit of the present disclosure. The above detailed description, therefore, is not to be taken in a limiting sense. For example, elements or features of one example, embodiment or implementation may be applied to any other example, embodiment or implementation described herein to the extent such contents do not conflict. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

The invention claimed is:

1. A method of qualifying a respiratory parameter of a patient, comprising:
positioning an infrared detector and an infrared projector exposed to a region of interest (ROI) of a patient;
projecting, by the infrared projector, an infrared feature onto the patient in the ROI;
measuring, by the infrared detector and utilizing the projected infrared feature, depth information comprising a distance between the patient and the infrared detector;
determining a first respiratory modulation signal of the patient comprising the depth information over time;
determining a second respiratory modulation signal of the patient using light intensity information in the ROI, over time, from the patient, wherein the second respiratory modulation signal is independent of the first respiratory modulation signal and is determined by:
measuring, by the infrared detector, a first reflected light intensity from the projected infrared feature at a first time;
measuring, by the infrared detector, a second reflected light intensity from the projected infrared feature at a second time subsequent to the first time; and
aggregating reflected light intensity information over time to create the second respiratory modulation signal; and
combining the first and second respiratory modulation signals to qualify a respiratory parameter of the patient, wherein the respiratory parameter comprises respiration rate.

2. The method of claim 1, wherein projecting the infrared feature onto the patient comprises:
projecting a pattern of individual features.

3. The method of claim 1, wherein projecting the infrared feature onto the patient comprises:
projecting a plurality of infrared features onto the patient.

4. The method of claim 1, wherein projecting the infrared feature onto the patient comprises:
projecting a grid or array of infrared features onto the patient in the ROI.

5. The method of claim 1, wherein the infrared camera comprises stereo first and second cameras, and wherein determining the second respiratory modulation signal comprises:
measuring the first reflected light intensity and the second reflected light intensity from the feature in stereo with the first camera and the second camera.

6. The method of claim 5, wherein measuring with the first camera and the second camera comprises:

comparing the first reflected light intensity measured by the first camera and the second camera to the second reflected light intensity measured by the first camera and the second camera.

7. The method of claim 1, further comprising phase-shifting the first or second respiratory signals prior to combining.

8. The method of claim 1, wherein the second respiratory modulation signal comprises an amount, color, or brightness of light over time.

9. A method of qualifying a respiratory rate of a patient, comprising:
  positioning first and second infrared cameras and an infrared projector exposed to a region of interest (ROI) of a patient;
  projecting, by the infrared projector, an IR feature pattern onto the ROI;
  acquiring, from the first and second infrared cameras, a depth image stream comprising depth images of the ROI over time;
  deriving a first respiratory signal from the depth image stream;
  acquiring, from at least one of the first and second infrared cameras, an IR light intensity stream comprising a light intensity of the projected IR feature pattern over time;
  calculating a second respiratory signal from the IR light intensity stream; and
  combining the first and second respiratory signals to provide an output respiratory rate.

10. The method of claim 9, wherein acquiring the IR light intensity stream comprises:
  measuring a first reflected light intensity from an IR feature at a first time;
  measuring a second reflected light intensity from the IR feature at a second time subsequent to the first time; and
  comparing the first reflected light intensity and the second reflected light intensity.

11. The method of claim 10, wherein measuring the first reflected light intensity and the second reflected light intensity comprises measuring the first reflected light intensity and the second reflected light intensity from the IR feature in stereo with the first camera and the second camera.

12. The method of claim 10, wherein acquiring the IR light intensity stream comprising the projected IR feature pattern comprises acquiring the IR light intensity stream from the non-contact patient monitoring system in the ROI.

13. The method of claim 12, wherein the non-contact patient monitoring system calculates the respiratory rate and derives the respiratory rate.

14. A method of determining a respiratory rate of a patient, comprising:
  projecting a pattern of infrared features onto a region of interest (ROI) of a patient, within a field of view of an infrared detector;
  acquiring a depth signal by measuring a distance between the ROI and the infrared detector, the depth signal comprising the measured distance over time;
  detecting, by the infrared detector, a light intensity of the projected pattern of infrared features and acquiring a light intensity signal comprising the detected light intensity over time; and
  combining the light intensity signal and the depth signal to calculate a respiratory rate.

15. The method of claim 14, wherein the infrared detector comprises a first camera and a second camera, and wherein detecting the light intensity of the projected pattern of infrared features comprises measuring a first reflected light intensity and a second reflected light intensity from the IR feature in stereo with the first camera and the second camera.

16. The method of claim 14, wherein:
  acquiring the light intensity signal and acquiring the depth signal comprises acquiring both signals from the infrared detector.

* * * * *